(12) United States Patent
Arnal

(10) Patent No.: US 10,806,556 B2
(45) Date of Patent: Oct. 20, 2020

(54) IMPLANT SHEATH SYSTEM HAVING A RELEASE FEATURE

(71) Applicant: Boston Scientific Scimed, Inc., Maple Grove, MN (US)

(72) Inventor: Kevin Arnal, Excelsior, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 283 days.

(21) Appl. No.: 15/136,976

(22) Filed: Apr. 24, 2016

(65) Prior Publication Data

US 2016/0310249 A1 Oct. 27, 2016

Related U.S. Application Data

(60) Provisional application No. 62/151,540, filed on Apr. 23, 2015, provisional application No. 62/151,467, filed on Apr. 23, 2015.

(51) Int. Cl.
*A61F 2/00* (2006.01)

(52) U.S. Cl.
CPC ...... *A61F 2/0045* (2013.01); *A61F 2240/001* (2013.01); *A61F 2250/006* (2013.01); *A61F 2250/0026* (2013.01); *A61F 2250/0065* (2013.01); *A61F 2250/0091* (2013.01)

(58) Field of Classification Search
CPC .......... A61F 2/0045; A61F 2/0095; A61F 2250/0063; A61F 2250/0065; A61F 2250/0021; A61F 2250/0025; A61F 2250/0026; A61F 2250/006; A61B 2017/00805; A61B 2018/00523

USPC ................................................ 600/29–31, 37
See application file for complete search history.

(56) References Cited

U.S. PATENT DOCUMENTS

| | | | | |
|---|---|---|---|---|
| 4,723,547 A * | 2/1988 | Kullas | .................. | A61F 5/0036 604/909 |
| 4,842,889 A * | 6/1989 | Hu | ........................ | B29C 59/14 427/296 |
| 4,957,477 A * | 9/1990 | Lundback | ........... | A61M 1/1068 600/16 |
| 5,112,344 A | 5/1992 | Petros | | |
| 5,188,589 A * | 2/1993 | Wypych | .............. | A61F 9/00745 604/22 |
| 5,611,515 A | 3/1997 | Benderev et al. | | |
| 5,736,251 A * | 4/1998 | Pinchuk | .................. | A61L 27/34 427/387 |
| 5,842,478 A | 12/1998 | Benderev et al. | | |
| 5,860,425 A | 1/1999 | Benderev et al. | | |
| 5,899,909 A | 5/1999 | Claren et al. | | |
| 6,039,686 A | 3/2000 | Kovac | | |
| 6,042,534 A | 3/2000 | Gellman et al. | | |
| 6,110,101 A | 8/2000 | Tihon et al. | | |
| 6,679,824 B1 * | 1/2004 | Reed | .................... | A61N 5/1027 600/7 |
| 2002/0151909 A1 * | 10/2002 | Gellman | .......... | A61B 17/00234 606/139 |
| 2002/0156487 A1 | 10/2002 | Gellman et al. | | |

(Continued)

*Primary Examiner* — Catherine B Kuhlman
(74) *Attorney, Agent, or Firm* — Brake Hughes Bellermann LLP

(57) ABSTRACT

An implant or sling sheath system having an overlapping sheath material is provided. The sheath can include two telescoping or overlapping sections. The overlapping sections can include at least one release feature to eliminate or reduce sticking of the overlapping sections together during use.

27 Claims, 3 Drawing Sheets

(56) References Cited

U.S. PATENT DOCUMENTS

| | | | | |
|---|---|---|---|---|
| 2005/0043580 A1* | 2/2005 | Watschke | ......... | A61B 17/06109 |
| | | | | 600/30 |
| 2009/0250588 A1* | 10/2009 | Robeson | ................ | H01L 29/06 |
| | | | | 249/187.1 |
| 2014/0052108 A1* | 2/2014 | De Kock | .......... | A61M 25/0009 |
| | | | | 604/528 |
| 2014/0173878 A1* | 6/2014 | Merk | ....................... | A61F 2/95 |
| | | | | 29/446 |

* cited by examiner

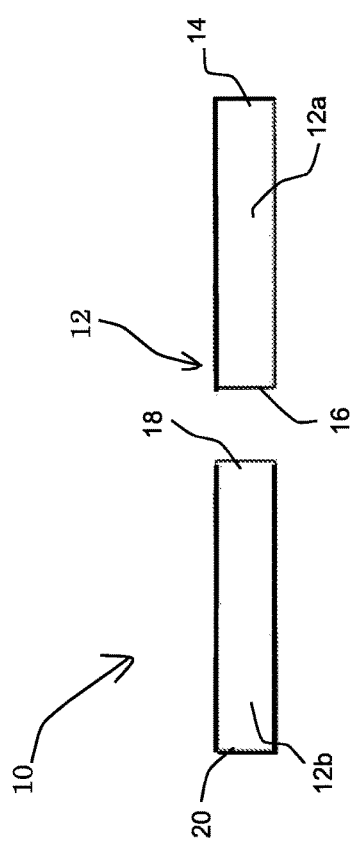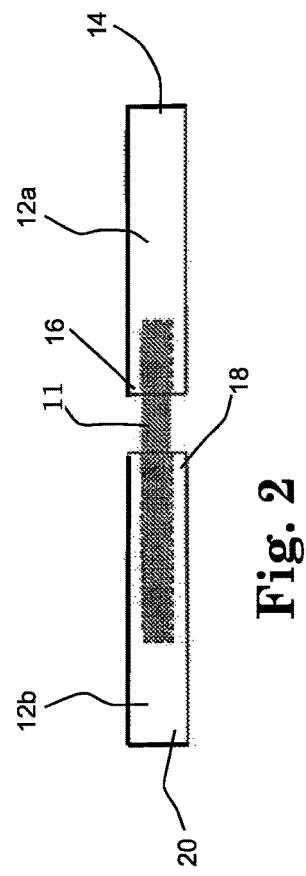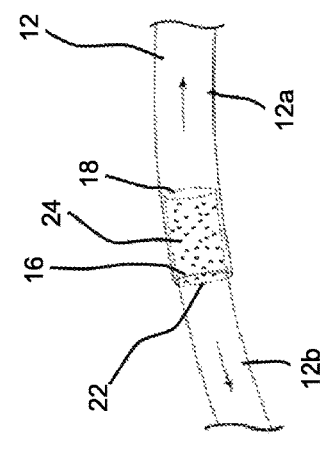

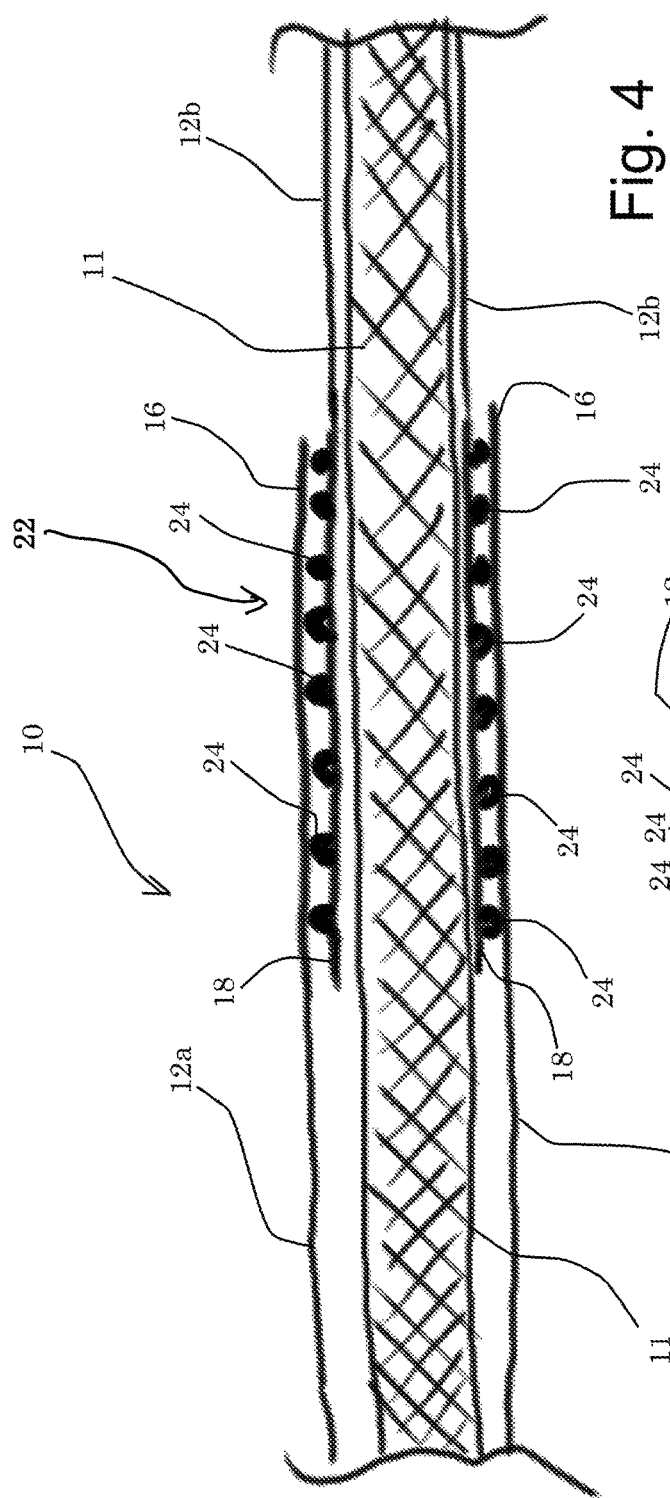

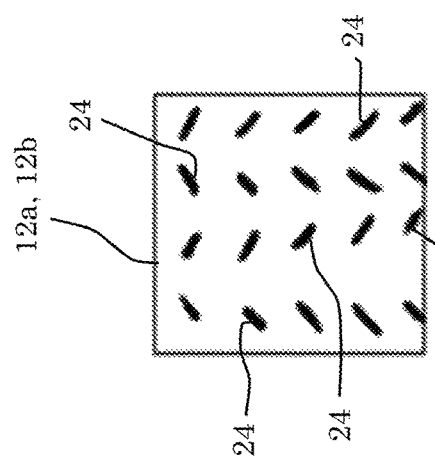
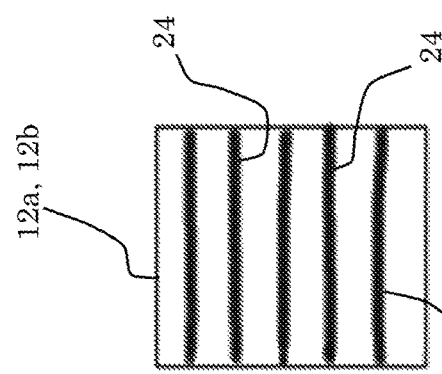
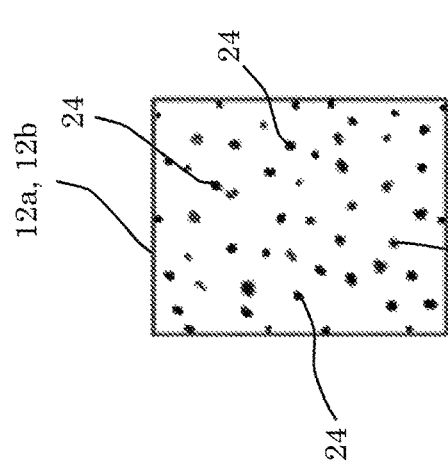
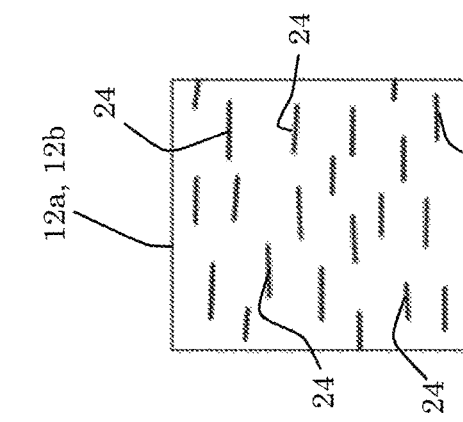
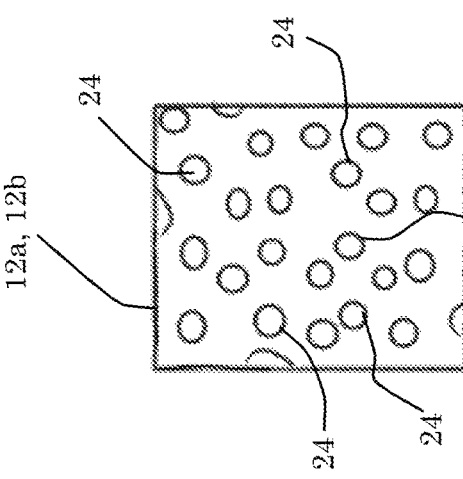
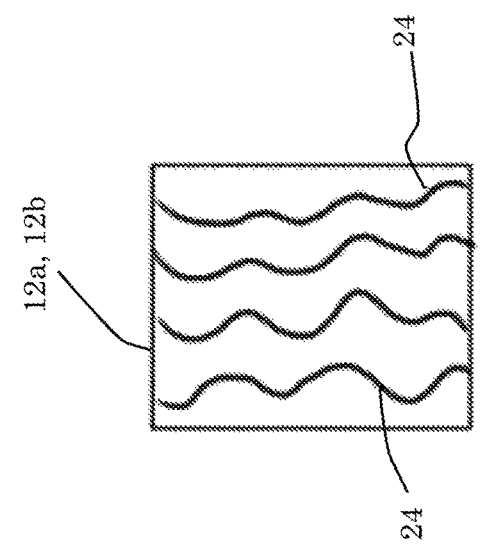

IMPLANT SHEATH SYSTEM HAVING A RELEASE FEATURE

PRIORITY

This Application claims priority to and the benefit of U.S. Provisional Patent Application No. 62/151,540, filed Apr. 23, 2015, and U.S. Provisional Patent Application No. 62/151,467, filed Apr. 23, 2015; with each of the referenced applications being incorporated fully herein by reference.

FIELD OF THE INVENTION

The invention relates generally to surgical devices and methods and, more particularly, to an implant or sling system having overlapping sheath sections that include one or more texture or like release features.

BACKGROUND OF THE INVENTION

Urinary incontinence is a significant health concern worldwide. Incontinence may occur when the pelvic floor weakens. There are five basic types of incontinence: stress incontinence, urge incontinence, mixed incontinence, overflow incontinence and functional incontinence. There are a large number of surgical interventions and procedures for addressing incontinence.

A variety of surgical procedure options are currently available to treat incontinence. Depending on age, medical condition, and personal preference, surgical procedures can be used to completely restore continence. One type of procedure, found to be an especially successful treatment option for SUI in both men and women, is a sling procedure.

A sling procedure is a surgical method involving the placement of a sling to stabilize or support the bladder neck or urethra. There are a variety of different sling procedures. Descriptions of different sling procedures are disclosed in U.S. Pat. Nos. 5,112,344; 5,611,515; 5,842,478; 5,860,425; 5,899,909; 6,039,686, 6,042,534 and 6,110,101.

Sling procedures differ in the type of material used for the sling, the method of anchoring the sling material in the body and how the sling material is inserted in the body. The time required for a surgical procedure varies, but is preferably as short as possible.

Many slings include a protective sheath used during insertion of the sling. After the sling is implanted, the sheath is removed and discarded. The protective sheath is generally constructed of a material that affords visual examination of the implantable sling and that affords smooth passage of the sling assembly through tissue of the patient. A two-piece overlapping sheath assembly is disclosed in published U.S. patent application Ser. No. 2002/0156487, which is hereby incorporated by reference fully herein.

In many cases, the sheath is made of polyethylene. Other materials used to construct the sheath include polypropylene, nylon, polyester or Teflon. The sheath material should be flexible and provide sufficient structural integrity to withstand the various forces exerted on the sheath throughout the sling delivery procedure. The sheath can be configured to have sufficient flexibility to facilitate user manipulation and adequate structural strength to withstand the various forces applied to the sheath during delivery and/or positioning of the sling assembly. It should also conveniently separate from the sling material after the sling is implanted without materially changing the position of the sling.

The sheath may comprise two elongate, separable sections. During sheath removal, the first section and the second section of the sheath are slid off the sling by pulling each end of the sheath away from the middle portion of the sling assembly. Removal of the sheath causes separation of the overlapping sheath sections, thereby exposing the sling.

However, with such configurations the first and second sections of the sheath can "stick" to one another or otherwise bind during the removal process due to either friction caused by the respective telescoping sections of the sheath or when a spacer such as a clamp is used under the urethra. This phenomenon can occur much like what occurs with highly polished gage blocks (e.g., which are very flat and can come into close contact across a relatively large surface area). As such, the sheaths can sometimes exhibit resistance to motion relative to one another.

SUMMARY OF THE INVENTION

The present invention relates generally to an implant or sling device including one or more sheath sections that are easily removed from a surgical sling after the sling assembly is situated under the patient's urethra or like anatomical structure of the patient. Various embodiments of the present invention can be employed with or by using existing or known incontinence sling materials, devices, or procedures.

In various embodiments of the present invention, a slight texture or surface feature can be provided to the sheath between the materials that interface with each other such that the materials resist or eliminate the behavior of resistance to motion. The texture or feature interferes with the material's surface interactions. The resulting value is that no other device or structural variable of the implant or sheath needs to change, other than the inside surface of the outer overlapping sheath, the outside of the inner overlapping sheath, or both. Because other operations are sometimes performed on the outside of the sheaths (printing, surface-surface bonding, etc.) it may be preferable to provide the surface texture on the inside of the outer overlapping sheath in certain embodiments.

The included release feature can include one or more ribs, nubs, generally linear or arcuate protrusions, longitudinal protrusions, undulations, periodic or spaced coatings, surface disruptions, rough surfaces, and the like.

BRIEF DESCRIPTION OF THE DRAWINGS

FIG. 1 shows a two-piece implant sheath assembly, in accordance with embodiments of the present invention.

FIG. 2 shows a two-piece implant sheath assembly shrouding portions of an implant, in accordance with embodiments of the present invention.

FIG. 3 shows an overlapping two-piece implant sheath assembly having a release feature, in accordance with embodiments of the present invention.

FIG. 4 shows an overlapping two-piece implant sheath assembly having a release feature and shrouding a portion of an implant, in accordance with embodiments of the present invention.

FIG. 5 shows an overlapping two-piece implant sheath assembly having a release feature, with the implant omitted, in accordance with embodiments of the present invention.

FIG. 6 shows adjacent inner and outer sheath sections with a release feature provided to the inside surface of an outer sheath section, in accordance with embodiments of the present invention.

FIG. 7 shows adjacent inner and outer sheath sections with a release feature provided to the outside surface of an inner sheath section, in accordance with embodiments of the present invention.

FIGS. 8-13 show partial views of exemplary release features provided to a target surface of an inner and/or outer sheath section, in accordance with embodiments of the present invention.

DETAILED DESCRIPTION OF PREFERRED EMBODIMENTS

Referring generally to FIGS. 1-13, the present invention is directed to an implant or sling system 10 having an overlapping sheath 12. The sheath 12 can include two telescoping or overlapping sections 12a, 12b. The sheath 12 is used during insertion of an implant or sling 11, during a medical procedure—e.g., treatment of a pelvic disorder in male or female patients. After the sling 10 is implanted, the sheath 12 is removed and discarded. The protective sheath 12 is generally constructed of a polymer material that affords visual examination of the implantable sling 11 (e.g., translucent) and that affords smooth passage of the sling assembly through tissue of the patient. In various embodiments, the present invention is directed to treating SUI, prolapse, and like pelvic conditions in women and men.

Various tools, device structures, implants, components, methods and techniques described and depicted in U.S. Patent Publication Nos. 2002/0156487 and 2005/0043580 are envisioned for use, in whole or in part, with the present invention. As such, the entire disclosures of the above-referenced patents are incorporated herein by reference in their entirety.

Referring to FIGS. 1-3, the two sheath or sleeve sections 12a, 12b enclose all or a portion of the implant 11. For example, the first sheath 12a has a proximal end 14 (which can include a release tab) and a distal end 16. The second sheath 12b has a proximal end 18 and a distal end 20. The distal end 16 of the first sheath 12a can be initially provided adjacent to the proximal end 18 of second sheath 12b.

The length of the sheaths 12a, 12b can vary greatly depending on the particular procedure or application. In certain embodiments the range can be from about 1.0 inches to about 16 inches. The first and second sheaths can be of equal length from their distal ends to proximal ends, or take on different length configurations. Any of the end portions 14, 16, 18, 20 can be tapered, thinner than other portions, or include a reduced inner and/or outer diameter compared to other sheath portions.

The proximal end 18 of sheath section 12b is inserted into the distal end 16 of sheath section 12a to form an overlap region 22 of the first and second sheaths 12a, 12b, as shown in FIG. 3. Similarly, the distal end 16 of section 12a can be inserted into the proximal end 18 of section 12b to define the overlap region 22 in particular embodiments.

The overlap region 22 may range in length from about 0.2 inches to about 4.0 inches in various embodiments. In certain embodiments the proximal end 18 is smaller in overall diameter or construct compared to the distal end 16 to further facilitate insertion and the corresponding overlapping at region 22. Other material and dimensional constructs are envisioned as well to accommodate the overall and can be implemented without deviating from the spirit and scope of the present invention.

As shown in FIGS. 3-5, a texture or like release feature 24 can be provided to the sheath section at least at the overlap region 22—where the materials 18, 16 interface with each other—such that the materials will not exhibit the behavior of resistance to motion. The feature 24 interferes with or alters the materials' surface interactions. This is beneficial because no other device or structural variable of the implant 11 or sheath 12 needs to change, other than the surface texture of the inside of the outer overlapping sheath 12a (FIG. 5—shown without the implant 11), the outside of the inner overlapping sheath 12b (FIG. 4), or both. Because other operations are sometimes performed on the outside of the sheaths (printing, surface-surface bonding, etc.) it may be preferable with certain embodiments to provide the surface texture or feature 24 on the inside of the outer overlapping sheath 12b. The feature 24 can be provided along a limited portion of the applicable sheath (e.g., ends 16 or 18) or along the entire length of either or both sheaths 12a, 12b.

FIGS. 6-7 show close-up views of a portion of the interaction region. The feature 24 is provided to an inner surface of sheath section 12a in FIG. 6. The feature 24 is provided to an outer surface of sheath section 12b in FIG. 7. The feature 24 of FIG. 6 includes a plurality of small surface disruptions or textures. The feature 24 of FIG. 7 includes undulating protrusions or members.

The release feature 24 can be provided with or applied to the target surface or sheath surface via various techniques or procedures. In certain embodiments, the feature 24 can be defined with the target sheath surface via a molding or extrusion process. In other embodiments, the feature 24 can be etched (e.g., via laser, cutting, surface disruption) or otherwise defined in or on the corresponding surface. Further, the feature 24 can be included on or in a separate material (e.g., film) and applied to the applicable target surface of the sheath—e.g., via adhesive, molding, sealing, melting, and the like. In still other embodiments, one or more elements, members, or textures can be formed or provided to the sheath surface by applying a generally viscous polymer or like material, spraying polymer or like material onto the sheath surface, etc.

FIGS. 8-13 depict various exemplary release features 24 provide to a surface of sheath sections 12a and/or 12b. The release features 24 can include one or more nubs (FIG. 12), generally linear or arcuate ribs (FIGS. 9, 10, 11, and 13), longitudinal protrusions (FIGS. 9 and 11), undulations (FIG. 11), periodic or spaced coatings, surface disruptions or rough surfaces (FIG. 8), and the like.

For instance, sheath 12 portions including ribs can include one or more ribs 24 placed on respective interfacing surfaces of the sheath 12. The ribs 24 (and any of the other feature 24 embodiments) can extend along the longitudinal axis of the sheath surface (FIG. 11), angled (FIG. 10), or transverse to the longitudinal axis (FIGS. 9 and 13). To facilitate the described release at the interface region, the features 24 can be provided on the inside surface of the outer sheath 12a. The outer surface of the inner sheath 12b can include the features 24 or can be provided smooth and without the feature 24. Again, a myriad of features 24 can be provided to promote the surface release benefits of the present invention, and can be provided along the entire length of the corresponding sheath section 12a, 12b, an area past the overlap region 22, or just at the overlap region 22.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What is claimed is:

1. An implant sheath system, comprising:
   a first sheath having a proximal portion and a distal portion defining a longitudinal line between the proximal portion and the distal portion of the first sheath, the first sheath having a first surface feature disposed on a portion of a surface of the first sheath and a second surface feature disposed on a portion of the surface of the first sheath, the first surface feature extending at an angle with respect to the longitudinal line of the first sheath, the second surface feature extending at an angle with respect to the first surface feature and at an angle with respect to the longitudinal line of the first sheath; and
   a second sheath having a proximal portion and a distal portion defining a longitudinal line between the proximal portion and the distal portion of the second sheath, the second sheath having a surface feature disposed on a portion of a surface of the second sheath, the proximal portion of the first sheath is insertable within the distal portion of the second sheath to define an overlapping interface region,
   the first surface feature and the second surface feature of the first sheath being configured to reduce material binding at the interface region.

2. The system of claim 1, wherein the surface feature of the second sheath is disposed on to an inner surface of the second sheath.

3. The system of claim 2, wherein the surface feature of the second sheath is disposed on the inner surface of the second sheath only at the distal portion of the second sheath.

4. The system of claim 2, wherein the surface feature of the second sheath is disposed on the inner surface of the second sheath to an area greater than the distal portion of the second sheath.

5. The system of claim 1, wherein the first surface feature of the first sheath is disposed on an outer surface of the first sheath.

6. The system of claim 5, wherein the first surface feature of the first sheath is disposed on the outer surface of the first sheath only at the proximal portion of the first sheath.

7. The system of claim 5, wherein the first surface feature of the first sheath is disposed on the outer surface of the first sheath to an area greater than the proximal portion of the first sheath.

8. The system of claim 1, wherein the surface feature of the second sheath includes one or more nubs.

9. The system of claim 1, wherein the surface feature of the second sheath includes one or more elongate surface protrusions.

10. The system of claim 1, wherein the surface feature of the second sheath is defined via a molding process.

11. The system of claim 1, wherein the surface feature of the second sheath is defined via an etching process.

12. The system of claim 1, wherein the surface feature of the second sheath is provided to a separate film material.

13. The system of claim 1, further including an implant shrouded at least in part by the first sheath and the second sheath.

14. The system of claim 1, wherein the surface feature of the second sheath includes one or more elongate surface protrusions that extend at an angle with respect to the longitudinal line of the second sheath.

15. An implant sheath system, comprising:
    a first sheath having a proximal portion and a distal portion defining a longitudinal axis between the proximal portion and the distal portion of the first sheath, the first sheath having a first surface feature disposed on a portion of a surface of the first sheath and a second surface feature disposed on a portion of the surface of the first sheath, the first surface feature extending at an angle with respect to the longitudinal axis of the first sheath, the second surface feature extending at an angle with respect to the first surface feature and at an angle with respect to the longitudinal axis of the first sheath;
    a second sheath having a proximal portion and a distal portion defining a longitudinal axis between the proximal portion and the distal portion of the second sheath, the second sheath having a surface feature disposed on a portion of a surface of the second sheath, the proximal portion of the first sheath is insertable within the distal portion of the second sheath to define an overlapping interface,
    the first surface feature of the first sheath and the second surface feature of the first sheath being configured to engage the second sheath at the interface region to reduce material binding of the proximal portion of the first sheath with the distal portion of the second sheath; and
    an implant shrouded at least by the interface region.

16. The system of claim 15, wherein the surface feature of the second sheath is disposed on an inner surface of the second sheath.

17. The system of claim 16, wherein the surface feature of the second sheath is disposed on the inner surface of the second sheath only at the distal portion of the second sheath.

18. The system of claim 16, wherein the surface feature of the second sheath is disposed on the inner surface of the second sheath to an area greater than the distal portion of the second sheath.

19. The system of claim 15, wherein the first surface feature of the first sheath is disposed on an outer surface of the first sheath.

20. The system of claim 19, wherein the first surface feature of the first sheath is disposed on the outer surface of the first sheath only at the proximal portion of the first sheath.

21. The system of claim 19, wherein the first surface feature of the first sheath is disposed on the outer surface of the first sheath to an area greater than the proximal portion of the first sheath.

22. The system of claim 15, wherein the surface feature of the second sheath includes one or more elongate surface protrusions.

23. The system of claim 15, wherein the surface feature of the second sheath is defined via a molding process.

24. The system of claim 15, wherein the surface feature of the second sheath is defined via an etching process.

25. The system of claim 15, wherein the surface feature of the second sheath is provided to a separate film material.

26. An implant sheath system, comprising:
    a first sheath having a proximal portion and a distal portion defining a longitudinal line between the proximal portion and the distal portion of the first sheath, the first sheath having a surface feature disposed on a portion of a surface of the first sheath; and
    a second sheath having a proximal portion and a distal portion defining a longitudinal line between the proximal portion and the distal portion of the second sheath, the second sheath having a first elongate surface protrusion disposed on a portion of a surface of the first sheath and a second elongate surface protrusion disposed on a portion of the surface of the second sheath, the first elongate surface protrusion extending at an angle with respect to the longitudinal line of the second sheath, the second elongate surface protrusion extending at an angle with respect to the first elongate surface protrusion and at an angle with respect to the longitudinal line of the second sheath, the proximal portion of the first sheath is insertable within the distal portion of the second sheath to define an overlapping interface region, the first elongate surface protrusion and the second elongate surface protrusion being configured to reduce material binding at the interface region.

27. The system of claim 26, wherein the surface feature of the first sheath includes one or more elongate surface protrusions that extend at an angle with respect to the longitudinal line of the first sheath.

\* \* \* \* \*